(12) United States Patent
Glorioso et al.

(10) Patent No.: US 9,616,382 B2
(45) Date of Patent: Apr. 11, 2017

(54) HUMIDITY CONTROL SYSTEM

(71) Applicant: DESICCARE, INC., Reno, NV (US)

(72) Inventors: Sammie Joe Glorioso, Ridgeland, MS (US); Benjamin Edward Blankenhorn, Reno, NV (US)

(73) Assignee: Desiccare, Inc., Reno, NV (US)

( * ) Notice: Subject to any disclaimer, the term of this patent is extended or adjusted under 35 U.S.C. 154(b) by 0 days.

(21) Appl. No.: 15/225,772

(22) Filed: Aug. 1, 2016

(65) Prior Publication Data

US 2017/0043293 A1 Feb. 16, 2017

Related U.S. Application Data

(60) Provisional application No. 62/203,788, filed on Aug. 11, 2015, provisional application No. 62/261,766, (Continued)

(51) Int. Cl.
*B01D 53/02* (2006.01)
*B01D 53/26* (2006.01)
(Continued)

(52) U.S. Cl.
CPC ....... *B01D 53/263* (2013.01); *B01D 53/0407* (2013.01); *B01J 20/02* (2013.01); *B01J 20/22* (2013.01); *B01J 20/261* (2013.01); *B01J 20/262* (2013.01); *B01J 20/28047* (2013.01); *B65D 65/42* (2013.01); *B65D 81/266* (2013.01); *B01D 2253/112* (2013.01); *B01D 2253/20* (2013.01);
(Continued)

(58) Field of Classification Search
CPC .......... B01D 2257/104; B01D 2257/80; B01D 53/28; B01J 20/043; B01J 20/045; B01J 20/046; B01J 20/103; B01J 20/20; B01J 20/28014; B01J 20/2803; B01J 20/28042; B01J 20/2805; B01J 20/3035; B01J 20/3042; B01J 20/3078; B01J 20/3204; B01J 20/3208; B01J 20/3212; B01J 20/3236; B01J 20/3293; B01J 2220/42; B01J 2220/46; B01J 2220/4843
See application file for complete search history.

(56) References Cited

U.S. PATENT DOCUMENTS 2,329,908 A * 9/1943 Johnson .................. A24F 25/02
206/204
4,151,304 A * 4/1979 Evans ...................... A61K 8/06
424/59

(Continued)

FOREIGN PATENT DOCUMENTS

EP 0835685 4/1998
KR 20050013986 5/2005

OTHER PUBLICATIONS

Swedberg, Claire "Smartrac's New Passive Sensor DogBone Transmits Moisture Levels", RFID Journal, Feb. 20, 2015, 2 pages. http;//www.rfidjournal.com/articles/view?12723.
(Continued)

*Primary Examiner* — Christopher P Jones
(74) *Attorney, Agent, or Firm* — Thomas J. Daly; Sami I. Schilly; Lewis Roca Rothgerber Christie LLP

(57) ABSTRACT

A humidity control system includes a humectant material, an oxygen absorbing composition, and a package housing the humectant material and the oxygen absorbing composition.

16 Claims, 9 Drawing Sheets

Related U.S. Application Data filed on Dec. 1, 2015, provisional application No. 62/261,768, filed on Dec. 1, 2015.

(51) Int. Cl.
| | |
|---|---|
| *B01J 20/02* | (2006.01) |
| *B01J 20/22* | (2006.01) |
| *B01J 20/26* | (2006.01) |
| *B01J 20/28* | (2006.01) |
| *B01D 53/04* | (2006.01) |
| *B65D 81/26* | (2006.01) |
| *B65D 65/42* | (2006.01) |

(52) U.S. Cl.
CPC .... *B01D 2253/25* (2013.01); *B01D 2257/104* (2013.01); *B01D 2257/80* (2013.01)

(56) References Cited

U.S. PATENT DOCUMENTS

| | | | | |
|---|---|---|---|---|
| 4,997,082 | A * | 3/1991 | Durocher | A24F 25/02 206/204 |
| 5,165,947 | A * | 11/1992 | Colucci | A23B 7/148 206/204 |
| 5,234,688 | A * | 8/1993 | Gaffar | A61K 8/24 206/524.1 |
| 5,346,604 | A * | 9/1994 | Van Sin | G01N 27/404 204/400 |
| 5,936,178 | A * | 8/1999 | Saari | A24F 25/02 84/453 |
| 5,975,288 | A * | 11/1999 | Crowder | A24F 25/02 206/205 |
| 6,039,892 | A * | 3/2000 | Himeshima | C09K 15/04 252/188.28 |
| 6,244,432 | B1 * | 6/2001 | Saari | A24F 25/02 206/213.1 |
| 6,716,276 | B2 | 4/2004 | Loop et al. | |
| 6,921,026 | B2 | 7/2005 | Saari et al. | |
| 6,977,589 | B2 | 12/2005 | Loop et al. | |
| 8,048,201 | B2 | 11/2011 | Dukes et al. | |
| 8,748,723 | B1 * | 6/2014 | Egberg | G10G 7/00 261/99 |
| 8,771,770 | B1 * | 7/2014 | Crump | B65D 81/28 206/204 |
| 9,050,410 | B2 * | 6/2015 | Mabuchi | A61L 2/087 |
| 2005/0145512 | A1 * | 7/2005 | Compton | G11B 23/021 206/308.1 |
| 2005/0162274 | A1 | 7/2005 | Shniberg et al. | |
| 2006/0097223 | A1 * | 5/2006 | Powers | B01D 53/28 252/194 |
| 2006/0263307 | A1 * | 11/2006 | Robillard | B32B 15/085 424/53 |
| 2007/0148213 | A1 * | 6/2007 | Ibrahim | A61K 8/0208 424/443 |
| 2007/0183936 | A1 * | 8/2007 | Newsam | B01L 3/5025 422/400 |
| 2008/0087599 | A1 * | 4/2008 | Mabuchi | A61L 2/087 210/500.23 |
| 2008/0173720 | A1 | 7/2008 | Kato et al. | |
| 2009/0028897 | A1 * | 1/2009 | Maestro | A61K 8/64 424/195.16 |
| 2009/0324752 | A1 * | 12/2009 | Lasserre | A61K 8/06 424/725 |
| 2010/0000414 | A1 * | 1/2010 | Williams | B01D 46/2414 96/226 |
| 2010/0209371 | A1 * | 8/2010 | Casado-Chaudanson | A61K 8/49 424/63 |
| 2012/0144906 | A1 | 6/2012 | Knyrim | |
| 2013/0185886 | A1 * | 7/2013 | Wood | A61F 13/15 15/244.4 |
| 2014/0069344 | A1 * | 3/2014 | Lipscomb | A01K 1/0107 119/171 |
| 2014/0154370 | A1 * | 6/2014 | Wood | A23B 7/154 426/118 |
| 2016/0018250 | A1 * | 1/2016 | Sollazzo Lee | G01G 13/02 222/1 |

OTHER PUBLICATIONS

Forney et al., "Control of Humidity in Small Controlled-environment Chambers using Glycerol-Water Solutions", Technology & Product Reports, Horticulture & Technology(2)1, pp. 52-54 Jan./Mar. 1992.

Pareek et al. Int J. Pharm Pharm Sci, vol. 6, Issue 6, Jul. 2014, 480-485.

Sud-Chemie, "Humidity Indicator Cards" Sud-Chemie Performance Packaging, 2003, pp. 1-2.

International Partial Search Report (Invitation to Pay Additional Fees) for International Application No. PCT/US2016/046643, mailed Nov. 21, 2016, 7 pages.

\* cited by examiner

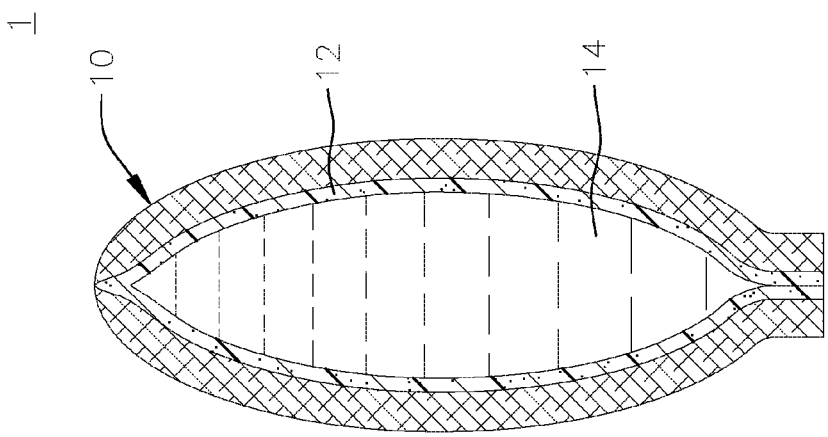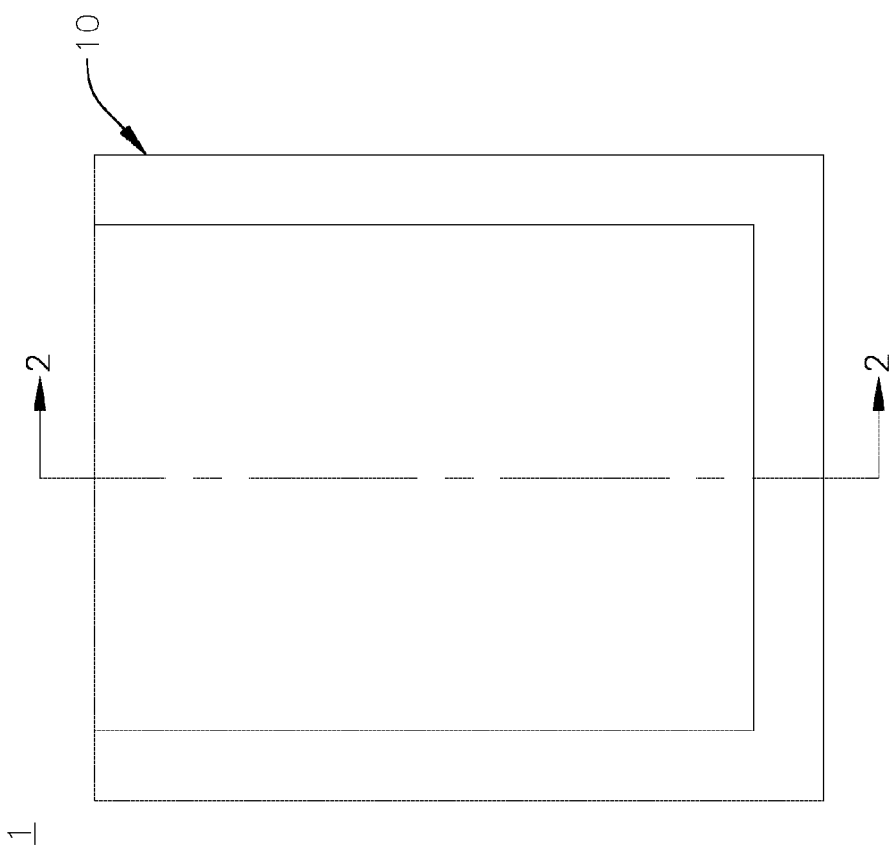

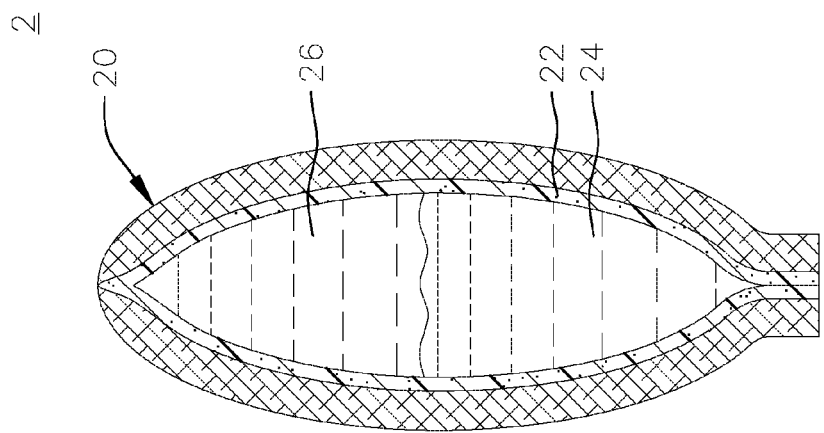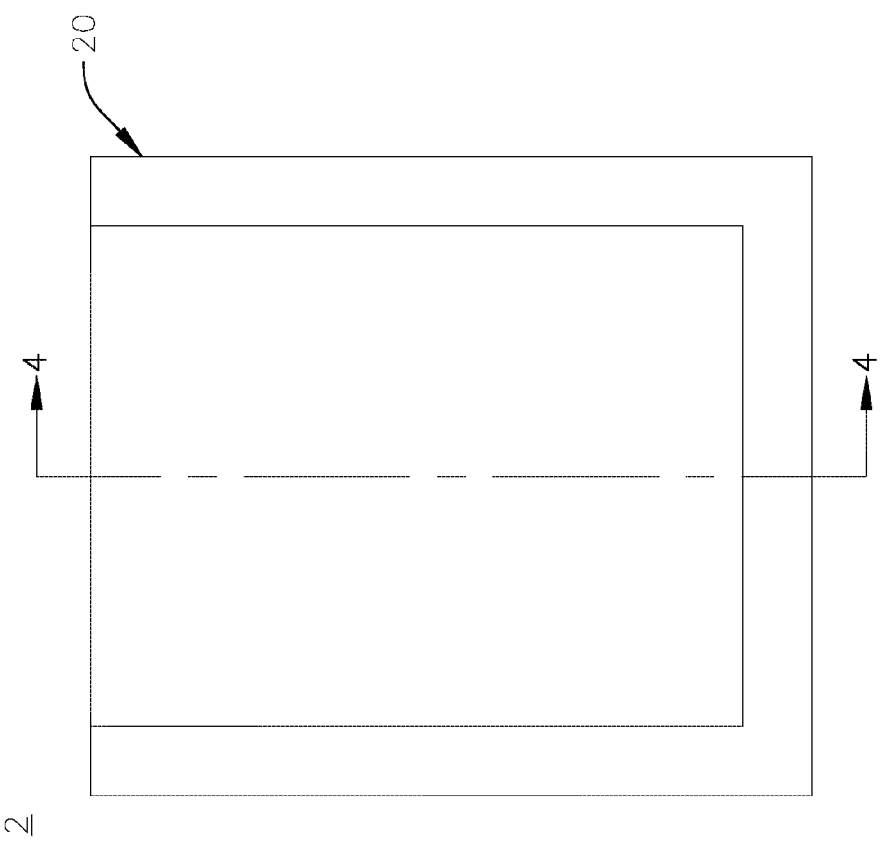

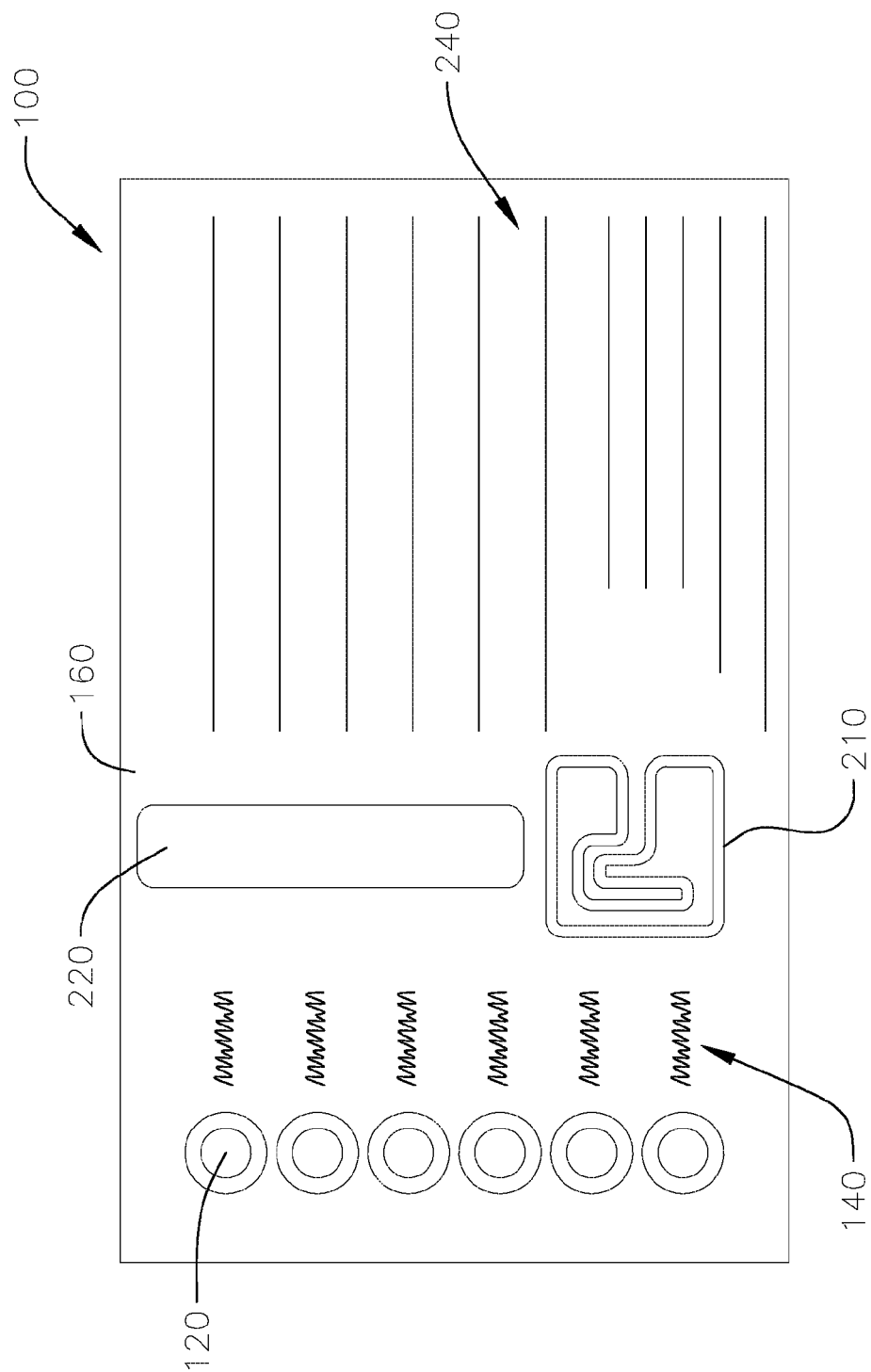

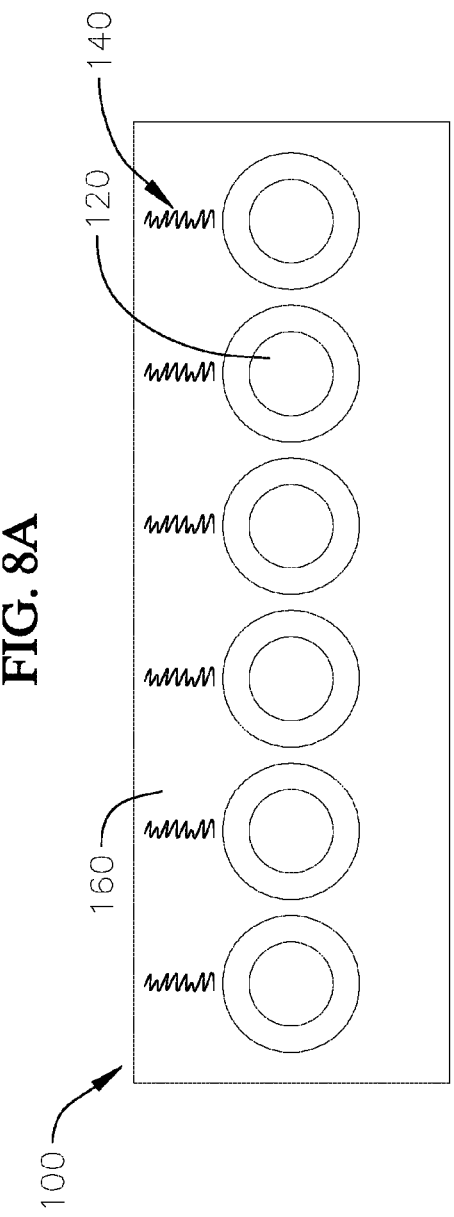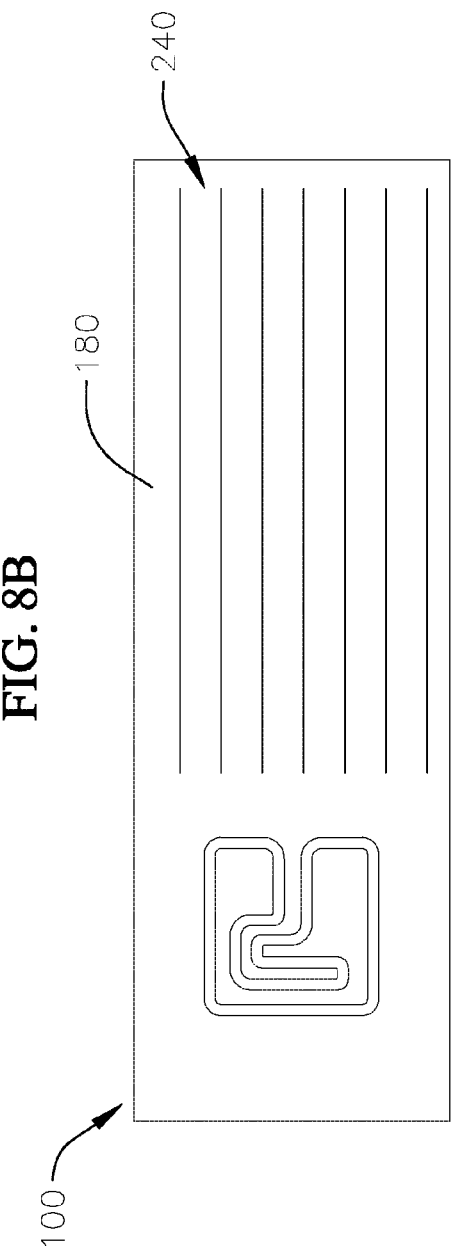

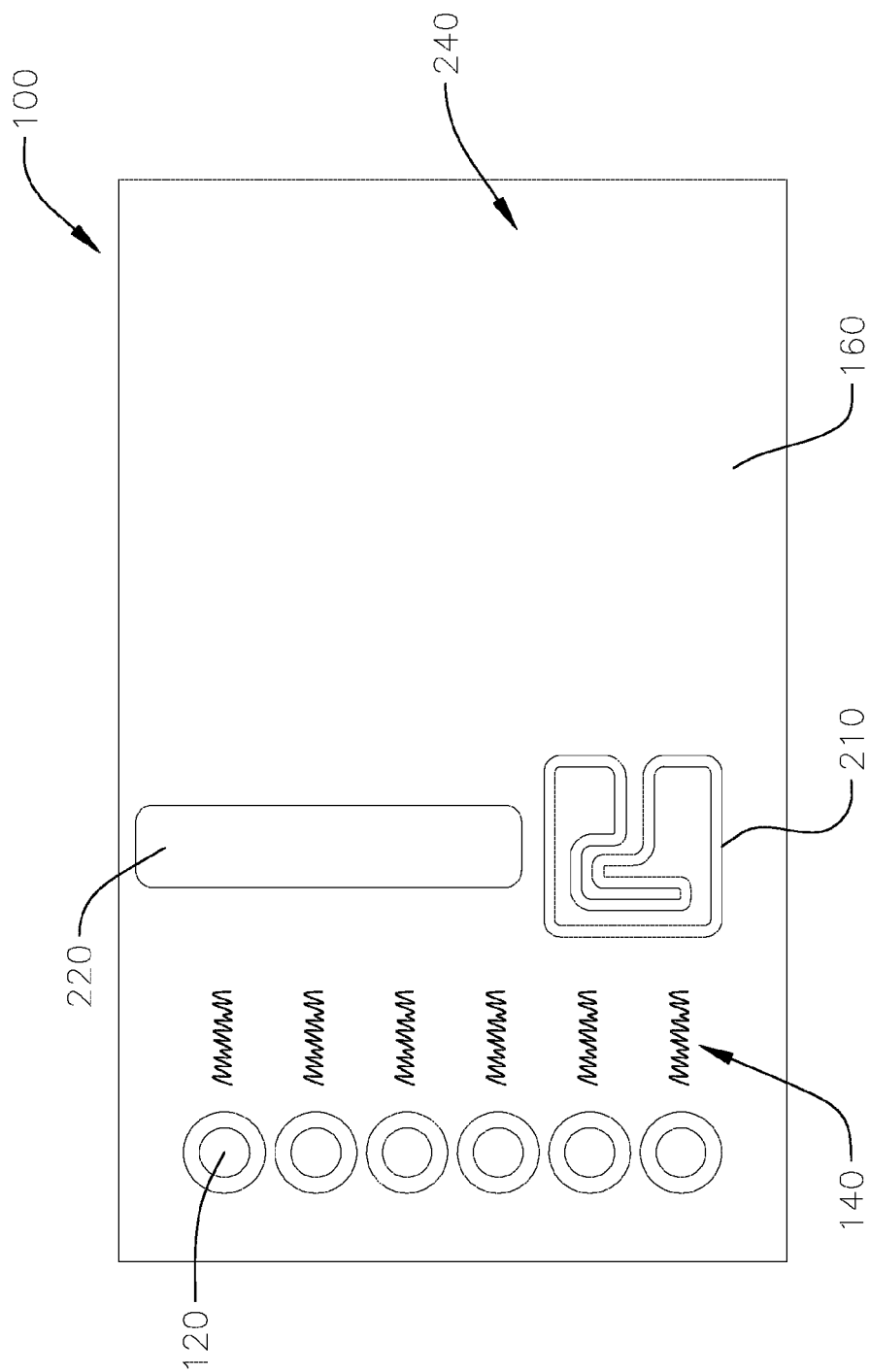

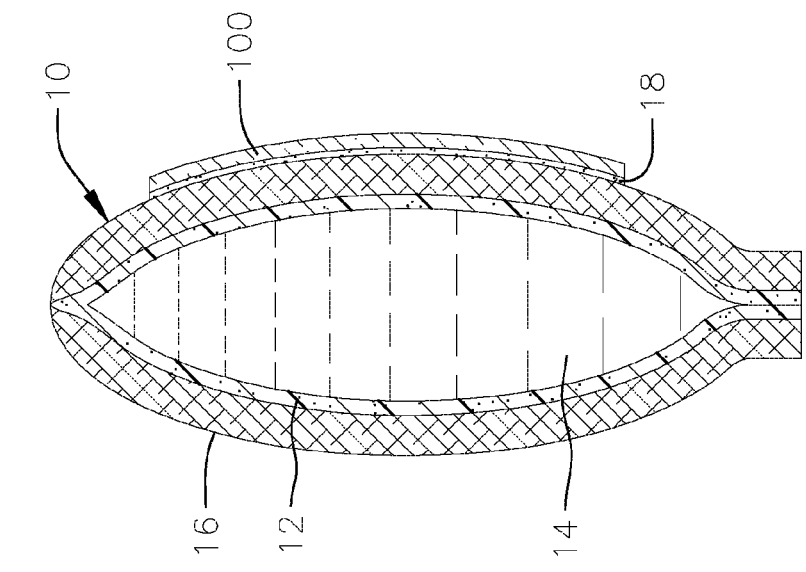
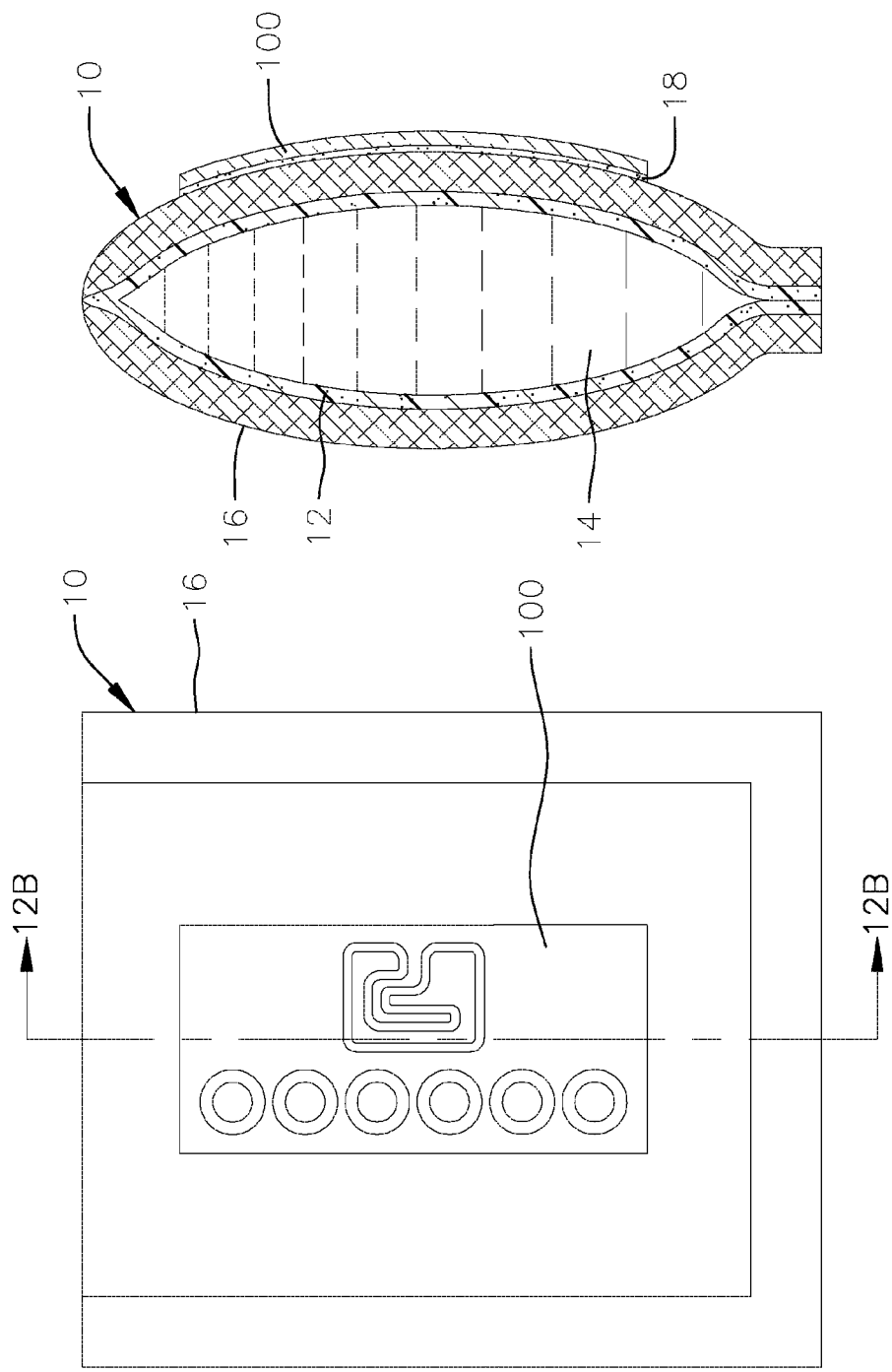
FIG. 12A
FIG. 12B

HUMIDITY CONTROL SYSTEM

CROSS-REFERENCE TO RELATED APPLICATION(S)

This application claims priority to and the benefit of U.S. Provisional Patent Application No. 62/203,788, filed in the United States Patent and Trademark Office on Aug. 11, 2015, U.S. Provisional Patent Application No. 62/261,766, filed in the United States Patent and Trademark Office on Dec. 1, 2015, and U.S. Provisional Patent Application No. 62/261,768, filed in the United States Patent and Trademark Office on Dec. 1, 2015, the entire contents of which are incorporated herein by reference.

BACKGROUND

1. Field

The present disclosure relates generally to the field of humidity control.

2. Description of Related Art

Humidity control products in general are well known. A humectant is a hygroscopic substance which is used to maintain moisture in an environment. Humectants that form the prior art often use saturated salt solutions to control humidity. However, the saturated salt solutions may emit an odor (e.g., an unpleasant odor) and often have a short life span (e.g., between about 30 to 45 days).

Oxygen control of various products, including food and pharmaceuticals, for example, is also desirable, because oxygen can be detrimental to food and pharmaceuticals and can advance spoilage of these products. Typical oxygen absorbers (or oxygen scavengers) use oxidation of iron or a similar metal to reduce oxygen in an environment, and require water to activate.

Often times, it is desirable to control both humidity and oxygen in the same environment. However, because oxygen absorbers often require water to activate, the oxygen absorber and humectant (or desiccant) must be separately packaged in order to maintain desired performance of both the oxygen absorber and the humectant/desiccant. As such, the humidity and oxygen controlling components may take up significant space in an enclosed environment (such as a pill bottle), thus reducing the amount of product that can be placed in the pill bottle or requiring the use of a relatively large pill bottle.

Humidity indicator cards (or HIC or humidity indicating cards) are designed to change color when the humidity level of an environment around the HIC exceeds or drops below a predetermined level. The HIC typically includes a visible indicator that indicates to a user when the humidity level of an environment exceeds or drops below a predetermined level. For example, the HIC may include a color-indicator that changes color when the HIC is exposed to a level of humidity that is greater than the predetermined level.

Humidity indicator cards are often used in contained environments. For example, an HIC is often placed in sealed packaging to provide a user means for determining and monitoring the humidity level inside of the packaging. Humidity indicator cards may be used in a wide variety of industries. For example, humidity indicator cards may be used in packaging for food, drugs, medical devices, and/or sensitive electronics. In some applications, for example when monitoring the humidity of tobacco and/or other drugs, it may be desirable for a user to monitor humidity of the product and its environment throughout the life of the product. In other applications, for example, produce shipments, the humidity indicator cards may be used when shipping to a wholesaler or retailer, but may be discarded prior to reaching the final intended user or consumer.

In some environments, surveillance and/or tracking of a product in addition to monitoring of humidity levels of the product may be desired. Various methods for surveillance, inventory tracking, traceability, security, and inventory management are known, including radio frequency identification (RFID) tags, ultrahigh frequency (UHF) sensors, electronic article surveillance (EAS) tags, electronic humidity recording tags and inlays (e.g., a SMARTRAC® DogBone RFID inlay), etc.

As an example, EAS tags, sometimes called source tags, are often used on high-value products. The EAS tags are normally deactivated (typically magnetically) at a checkout counter, but if not deactivated, a shoplifted product is detected at a store's exit to alert security personnel. Typically, EAS tags are placed on the product or on the inside or outside of a product carton (or on the outside of a product container such as a pharmaceutical bottle) where it may be detected and surreptitiously removed by an experienced shoplifter. However, placement of an exposed tag directly within certain types of products, such as foods or drugs, is unacceptable in view of FDA and other regulations which sharply limit the materials permitted to contact such products. Further, because the EAS tags often use one of acoustic-magnetic, radio frequency, microwave, and electromagnetic technology, it is generally undesirable to place the EAS tags in an environment having any moisture. Similar issues arise with the use of RFID, UHF, electronic humidity indicating inlays, and other similar tags or sensors.

SUMMARY

One or more embodiments of the present disclosure provide a humectant and an oxygen-absorber in one package, thereby controlling moisture within an environment and removing oxygen from the controlled moisture environment.

According to one or more embodiments of the present disclosure, a humidity control system includes a humectant material, an oxygen absorbing composition, and a package housing the humectant and the absorbing composition.

The package may define a single cavity that houses the humectant material and the oxygen absorbing composition.

The humidity control system may further include a coating layer between the package and the humectant material and the oxygen absorbing composition.

The coating may include a microporous coating.

The coating may include polyethylene, oriented polystyrene, a porous polyethylene resin, polyurethane, a polyether block amide, and/or a polymeric mixture comprising a hydrophilic monomer.

The coating may have a thickness from between about 0.001 inch and about 0.01 inch.

The package may include kraft paper having a basis weight of 30 lbs/msi.

The package may include an elastomeric polymer.

The oxygen absorbing composition may include a fatty oil and a transition metal enhancer.

The transition metal enhancer may include chromium, manganese, cobalt, iron, copper, and/or zinc.

The fatty oil may include an unsaturated fatty acid.

The unsaturated fatty acid may include an oleic acid and/or a linoleic acid.

The fatty oil may include a vegetable oil including triglycerides.

The vegetable oil may include linseed oil, soybean oil, and/or flaxseed oil.

The humectant material may include a water salt solution or a water salt gel.

The humectant material may include a viscous miscible glycerol and water mix.

The humectant material may further include a gelling agent.

The gelling agent may include gelatin, xanthan, alginate, and/or pectin.

The humidity control system may include lemon oil.

According to one or more embodiments of the present disclosure, an oxygen absorbing composition includes an unsaturated fatty acid and a transition metal enhancer.

BRIEF DESCRIPTION OF THE DRAWINGS

These and other features and aspects of embodiments of the present disclosure will be better understood by reference to the following detailed description, when considered in conjunction with the accompanying drawings. The same numbers are used throughout the figures to reference like features and components. The figures are schematic in nature and may not be drawn to scale.

FIG. 1 is a front elevational view of a humectant bag according to one or more embodiments of the present disclosure;

FIG. 2 is a sectional view taken along the line 2-2 of FIG. 1;

FIG. 3 is a front elevational view of a humectant and oxygen absorber according to one or more embodiments of the present disclosure;

FIG. 4 is sectional view taken along the line 4-4 of FIG. 3;

FIG. 7 is a front view of a humidity indicating card according to one or more embodiments of the present disclosure;

FIG. 8A is a front view of a humidity indicating card according to one or more embodiments of the present disclosure;

FIG. 8B is a back view of the humidity indicating card of FIG. 8A;

FIG. 9 is a front view of a humidity indicating card according to one or more embodiments of the present disclosure;

FIG. 12A is a front view of a humidity controller with a humidity indicating card affixed thereto; and FIG. 12B is a sectional view taken along the line 12B-12B of FIG. 12A.

DETAILED DESCRIPTION

Figure 6:
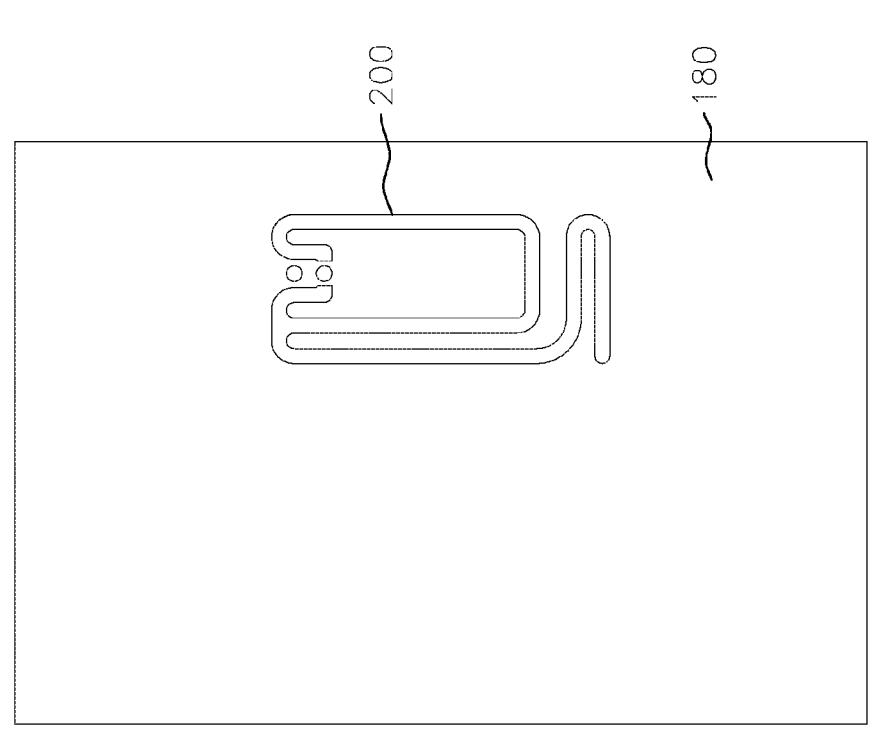
FIG. 6 is a back view of the humidity indicating card of FIG. 5.

Referring to FIGS. 1 and 2, a humectant system 1 includes a humectant bag (or pouch) 10 filled with a humectant material 14. The humectant bag 10 is made of a porous material which is permeable to vapor, and will pass vapor, but is impervious to liquid, dust and other particulates. For example, in one or more embodiments, kraft paper having a basis weight of 30 lbs/msi (pounds per 1,000 square inches) or more is used for the humectant bag 10. As another example, the humectant bag may be an elastomeric polyester.

The humectant bag 10 includes a coating 12 (e.g., a microporous coating) between the humectant bag 10 and the humectant material 14. The coating 12 is selected such that it provides adequate moisture vapor transmission (MVT) and seals the humectant bag 10. In other words, the coating 12 is also used as an adhesive to join together opposing sides of the humectant bag 10. The coating 12 also reduces or minimizes the likelihood of leakage of the humectant material 14 through the humectant bag 10. The coating 12 may be polyethylene, oriented polystyrene, a porous polyethylene resin, polyurethane, a polyether block amide, and/or a polymeric mixture including a hydrophilic monomer. The coating 12 prevents or reduces the likelihood of the humectant material 14 leaking from the humectant bag 10.

The coating 12 may be compliant with the Food and Drug Administration (FDA) standards, e.g., the regulations as stated in the Code of Federal Regulations, Title 21. For example, the coating 12 may omit any raw materials that are not included in the applicable sections of title 21 of the Code of Federal Regulations. The thickness of the coating may range from between about 0.001 inch and 0.01 inch, preferably between about 0.001 inch and 0.002 inch, and more preferably 0.001 inch. As shown in Table 1, at varying thicknesses of the coating 12, the water vapor transmission rate (VVVTR) of the humectant system may vary from about 16 g/100 sq. in/day to about 42 g/100 sq. in/day.

TABLE 1

| Thickness (inches) | FDA Compliant? | WVTR (g/100 sq. in/day) |
| --- | --- | --- |
| 0.001 | Yes | 28 |
| 0.002 | Yes | 16 |
| 0.001 | No | 42 |
| 0.002 | No | 18 |

The humectant bag 10 is filled with about 0.28 ounces (for the illustrated bag size of about 2 to 2½ inches high and about 2½ to 2¾ inches wide) of the humectant material 14. The humectant material 14 includes a viscous miscible glycerol (or glycerin) and water mix. In some embodiments, the humectant bag 10 may be between about 6 inches high and 4 inches wide and may be filled with about 2.12 ounces of the humectant material 14.

In some embodiments, the humectant material 14 also includes a gelling agent. The gelling agent may be a food hydrocolloid. For example, the gelling agent may be any one of gelatin, xanthan, alginate, and/or pectin. The gelling agent may increase viscosity of the humectant material 14 and may reduce or minimize the likelihood of the humectant material 14 leaching through the coating 12 and the humectant bag 10.

The glycerol and water mix of the humectant material 14 may range from about 70% to about 90% by weight glycerol. As such, the humectant material 14 may be suitable for monitoring humidity ranges of between about 30% and about 70% at temperatures of between about 68 degrees F. and 77 degrees F.

For example, to maintain a 60 relative humidity (RH) environment, the humectant material 14 may be formed of 25.0% (by weight) water, 1.0% gel, and 74.0% glycerol that are mixed together at 90 degrees Fahrenheit. As another example, to maintain a 50 RH environment, the humectant material 14 may be formed of 20% (by weight) water, 1.0% gel, and 79% glycerol that are mixed together at 90 degrees Fahrenheit. As yet another example, to maintain a 62 RH environment, the humectant material 14 may be formed of 27.67% (by weight) water, 0.97% gel, and 71.36% glycerol mixed together at 85 degrees Fahrenheit. The concentration of component materials in the humectant material 14 and the temperature at which they are combined each affect the performance characteristics of the humectant material 14. As such, the humectant material 14 may be prepared at a temperature of between about 85 degrees Fahrenheit and about 100 degrees Fahrenheit, with the concentration of component materials being scaled up according to the mixing temperature. If the component materials of the humectant material 14 are processed at a temperature above about 100 degrees Fahrenheit, the viscosity of the humectant material 14 may be reduced and the humectant material 14 may be more likely to leak through the humectant bag 10. In addition, the concentration of gel is typically around 1% (e.g., between about 0.9% and about 1.1%) to minimize or reduce the likelihood of leaking.

The humectant material 14, the coating 12, and the humectant bag 10 are nontoxic. As such, the humectant system 1 may be easily disposed of when the humectant system 1 shows exhaustion (e.g., a humidity indicating card (HIC) 100 adjacent the humectant system may change color, for example, from pink to violet) or has stopped adequately performing. The humectant bag 10 is easily stored, handled, and placed in service, and provides a convenient, effective and economical means for humidity control. Further, the humectant system 1 may have an enhanced life span (e.g., about four months) and may not emit an odor (e.g., an unpleasant odor).

Referring to FIGS. 3 and 4, a humectant and oxygen scavenger (or oxygen absorber) system 2 includes a package 20, an oxygen absorbing composition 26, and a humectant material 24.

In one or more embodiments, the package (or pouch or bag) 20, much like the package 10 described above, is made of a porous material which is permeable to vapor, and will pass vapor, but is impervious to liquid, dust and other particulates. For example, in one or more embodiments, kraft paper having a basis weight of 30 lbs/msi (pounds per 1,000 square inches) or more is used for the package 20. As another example, the humectant bag may be an elastomeric polyester.

In some embodiments, the package 20 includes a coating 22 (e.g., a microporous coating) between the package 20 and the oxygen absorbing composition 26 and the humectant material 24. The coating 26, much like the coating 12 described above, is selected such that it provides adequate moisture vapor transmission (MVT) and seals the package 20. In other words, the coating 22 is also used as an adhesive to join together opposing sides of the package 20. The coating 22 also reduces or minimizes the likelihood of leakage of the humectant material 24 and the oxygen absorbing composition 26 through the package 20. The coating 22 may be polyethylene, oriented polystyrene, a porous polyethylene resin, polyurethane, a polyether block amide, and/or a polymeric mixture including a hydrophilic monomer. The coating 22 prevents or reduces the likelihood of the humectant material 24 and the oxygen absorbing composition 26 leaking from the package 20.

The coating 22 may be compliant with the Food and Drug Administration (FDA) standards, e.g., the regulations as stated in the Code of Federal Regulations, Title 21. For example, the coating 22 may omit any raw materials that are not included in the applicable sections of title 21 of the Code of Federal Regulations. The thickness of the coating 22 may range from between about 0.001 inch and 0.01 inch, preferably between about 0.001 inch and 0.002 inch, and more preferably 0.001 inch. As shown in Table 1, above, at varying thicknesses of the coating 22, the water vapor transmission rate (VVVTR) of the humectant system may vary from about 16 g/100 sq. in/day to about 42 g/100 sq. in/day.

In one or more embodiments, the oxygen absorbing composition 26 uses an unsaturated fatty acid and a transition metal enhancer to promote oxygen removal. For example, the transition metal may include at least one of chromium (Cr), manganese (Mn), cobalt (Co), iron (Fe), copper (Cu), and zinc (Zn), alone or in combination. The unsaturated fatty acid may include at least one of an oleic acid, a linoleic acid, and the like, alone or in combination. Fatty oils including unsaturated fatty acids, such as vegetable oils including large quantities of triglycerides such as linseed oil, soybean oil, flaxseed oil, and the like may also be used for the oxygen absorbing composition 26. It will be appreciated that because the oxygen absorbing composition 26 according to one or more embodiments of the present invention does not require water to activate, performance of the oxygen absorbing composition 26 is not hindered by the humectant material 24 and performance of the humectant material 24 is not hindered by the oxygen absorbing composition 26.

The humectant material 24 may be any suitable humectant composition. For example, in some embodiments, any humectant including water salt solutions and/or gels may be utilized. In some embodiments, the humectant material 24 includes a viscous miscible glycerol (or glycerin) and water mix, much like the humectant material 14 described above. In some embodiments, the humectant material 24 also includes a gelling agent. The gelling agent may be a food hydrocolloid. For example, the gelling agent may be any one of gelatin, xanthan, alginate, and/or pectin. The gelling agent may increase viscosity of the humectant material 24 and may reduce or minimize the likelihood of the humectant material 24 leaking through the coating 22 on the package 20 and/or through the package 20.

The glycerol and water mix of the humectant material 24 may range from about 70% to about 90% by weight glycerol. As such, the humectant material 24 may be suitable for monitoring humidity ranges of between about 30% and about 70% at temperatures of between about 68 degrees F. and 77 degrees F.

For example, to maintain a 60 relative humidity (RH) environment, the humectant material 24 may be formed of 25.0% (by weight) water, 1.0% gel, and 74.0% glycerol that are mixed together at 90 degrees Fahrenheit. As another example, to maintain a 50 RH environment, the humectant material 24 may be formed of 20% (by weight) water, 1.0% gel, and 79% glycerol that are mixed together at 90 degrees Fahrenheit. As yet another example, to maintain a 62 RH environment, the humectant material 24 may be formed of 27.67% (by weight) water, 0.97% gel, and 71.36% glycerol mixed together at 85 degrees Fahrenheit. The concentration of component materials in the humectant material 14 and the temperature at which they are combined each affect the performance characteristics of the humectant material 24. As such, the humectant material may be prepared at a temperature of between about 85 degrees Fahrenheit and about 100 degrees Fahrenheit, with the concentration of component materials being scaled up according to the mixing temperature. If the component materials of the humectant material 24 are processed at a temperature above about 100 degrees Fahrenheit, the viscosity of the humectant material 24 may be reduced and the humectant material 24 may be more likely to leak through the humectant bag 10. In addition, the concentration of gel is typically around 1% (e.g., between about 0.9% and about 1.1%) to minimize or reduce the likelihood of leaking.

The humectant material 24, the coating 22, the package 20, and the oxygen absorbing composition 26 are nontoxic. As such, the humectant and oxygen scavenger system 2 may be easily disposed of when the humectant and oxygen scavenger system 2 shows exhaustion (e.g., when a humidity indicating card (HIC) 100 adjacent the humectant and oxygen scavenger system 2 may change color, for example, from pink to violet) or has stopped adequately performing. The package 20 is easily stored, handled, and placed in service, and provides a convenient, effective and economical means for humidity control. Further, the humectant system may have an enhanced life span (e.g., about four months) and may not emit an odor (e.g., an unpleasant odor).

The humectant and oxygen scavenger system 2 may also include scented materials, such as lemon oil, which lend a pleasant aroma to the space in which the humectant and oxygen scavenger is placed.

In one example embodiment, the humectant and oxygen scavenger system 2 includes 10 grams of flax oil, 10 drops of manganese napthenate, and 40 grams of a zeolite carrier and 17 grams of the 60 RH humectant gel. In trial experiments, this embodiment has exhibited maintenance of 60 RH and absorbed 200 cc of oxygen over 24 hours, and total absorption of 400 cc. In some embodiments, lemon scent may be added to the humectant and oxygen scavenger system 2.

In another example embodiment, the humectant and oxygen scavenger system 2 includes 10 grams of flax oil, 5 drops of zirconium, and 40 grams of a zeolite carrier and 17 grams of the 60 RH humectant gel.

According to one or more example embodiments of the present disclosure, the oxygen absorbing composition 26 and the humectant material 24 are included in a single package 20. For example, an inner surface of the package 20 may be coated with the coating 22, then the humectant material 24 may be inserted into the package 20, then the oxygen absorbing composition 26 may be inserted into the package 20, and then the package 20 may be sealed. In some embodiments, the inner surface of the package 20 may be coated with the coating 22, then the oxygen absorbing composition 26 may be inserted into the package 20, then the humectant material 24 may be inserted into the package 20, and then the package 20 may be sealed. In yet further embodiments, the oxygen absorbing composition 26 and the humectant material 24 may be mixed together and then inserted into the package 20. Although the oxygen absorbing composition 26 and the humectant material 24 may be included in one package, the oxygen absorbing composition 26 may still absorb oxygen from the surrounding environment and the humectant material 24 may still maintain moisture in the surrounding environment.

One or more embodiments of the present disclosure are directed to a humidity indicating card (or HIC or humidity indicator card) 100 that allows for inventory tracking, traceability, security, and/or inventory management. The humidity indicating card 100 may be used in an enclosed or substantially enclosed environment.

Figure 5:
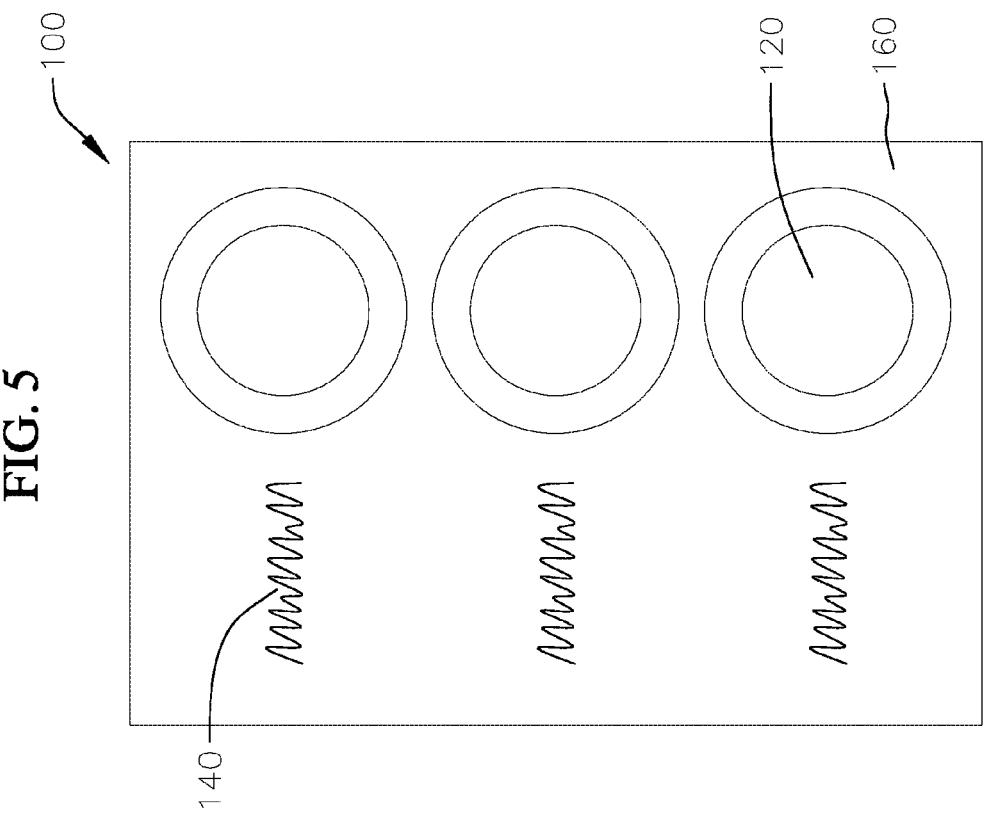
FIG. 5 is a front view of a humidity indicating card according to one or more embodiments of the present disclosure.

Referring to FIGS. 5 and 6, the HIC 100 has a front surface 160 and a back surface 180. In one or more embodiments, the front surface 160 includes one or more indicators 120 that change color according to a level of humidity in the environment surrounding the HIC 100. For example, in some embodiments, the HIC 100 includes three indicators 12 that change color from blue to pink according to the humidity level in the surrounding environment. The HIC 100 may also include a label 140 that indicates the humidity percentages and associated colors for the indicators 120. The HIC 100 may be made of a fiber composite, for example, cellulose, starch, and/or resin, and the indicators 120 may be made of cobalt chloride, cobalt salts, bromide salt, and/or an indicating dye, for example. It will be appreciated that in some embodiments, the HIC 100 may include one or more stacked sheets (e.g., fiber composite sheets).

As illustrated in FIG. 6, in one or more embodiments, the HIC 100 further includes a radio frequency identification device (RFID) 200 attached to the HIC 100. In one or more embodiments, the RFID 200 is attached to the back surface 180 of the HIC 100, and in some embodiments, the RFID 200 is attached to the front surface 160 of the HIC 100. As discussed in greater detail below, in some embodiments, the RFID 200 may be embedded between adjacently stacked sheets of the HIC 100. The RFID 200 includes a magnetic strip. The RFID 200 enables tracking of the HIC 100, thereby enhancing security and inventory management of the HIC 100 and any product packaging that includes the HIC 100.

Figure 10A:
FIG. 10A is a cross-sectional side view of a humidity indicating card according to one or more embodiments of the present disclosure.
Figure 10B:
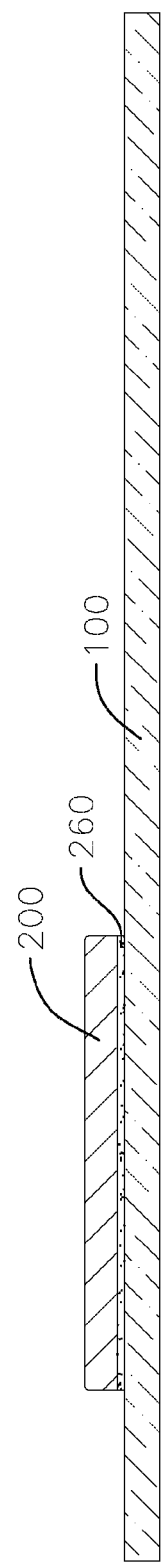
FIG. 10B is a cross-sectional side view of a humidity indicating card according to one or more embodiments of the present disclosure.

As illustrated in FIGS. 10A and 10B, the RFID 200 may be affixed to the HIC 100 by an adhesive, for example, by a double-sided tape, a single-sided tape, a printed tag, an adhesive backing, and/or a hot melt adhesive (or a hot melt glue). For example, the RFID 200 may be affixed to the HIC 100 by a hot melt adhesive 260 or by a single-sided tape 280.

In embodiments where the RFID 200 is affixed to the HIC 100 by a hot melt adhesive 260 (or a double-sided tape or other similar bottom-affixing adhesive), the hot melt adhesive 260 may be applied to at least a periphery of the RFID 200 on a bottom or lower surface of the RFID 200. As such, the bottom surface of the RFID 200 is uniformly or substantially uniformly flush with the corresponding surface of the HIC 100, thus eliminating or substantially eliminating any openings or gaps that may form between the RFID 200 and the HIC 100. As such, when the HIC 100 having the RFID 200 is placed into a package or container 300 (see FIG. 11) or other enclosed environment having a product housed therein, the product does not become trapped between the RFID 200 and the HIC 100.

Similarly, in embodiments where the RFID 200 is affixed to the HIC 100 by the single-sided tape 280 (or a printed tag or other similar top-affixing adhesive), the single-sided tape 280 may surround an entire top or upper surface of the RFID 200, and may extend beyond each edge of the RFID 200, for example, by two mm or more. As such, the single-sided tape 280 seals the RFID 200 to the HIC 100 and eliminates or substantially eliminates any openings or gaps that may otherwise form between the RFID 200 and the HIC 100 and/or between the RFID 200 and the single-sided tape 280.

As such, when the HIC 100 having the RFID 200 is placed into the container 300 (see FIG. 11) or other enclosed environment having a product housed therein, the product does not become trapped between the RFID 200 and the HIC 100 or the single-sided tape 280.

Figure 10C:
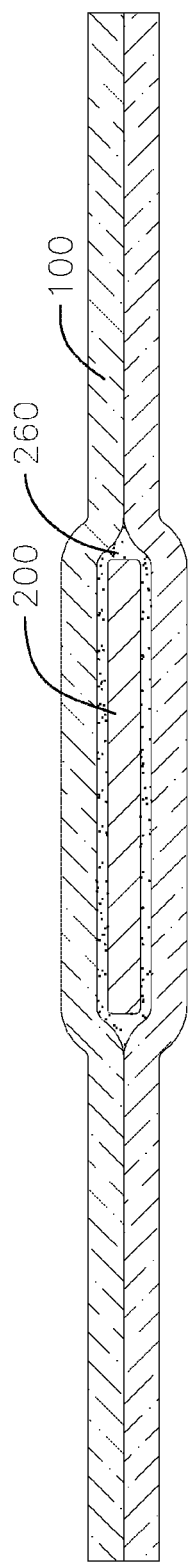
FIG. 10C is a cross-sectional side view of a humidity indicating card according to one or more embodiments of the present disclosure.

As yet another example, as illustrated in FIG. 10C, in some embodiments the RFID 200 may be embedded or affixed between adjacently stacked layers of the HIC 100. In such embodiments, the RFID 200 may be affixed to the HIC 100 by a bottom-fixing adhesive and/or a top-fixing adhesive. As such, the RFID 200 may be difficult to remove from the HIC 100 without tearing or otherwise visibly tampering with the HIC 100. Further, because the RFID 200 is not on an outer surface of the HIC 100, the product is not likely to become trapped between the RFID 200 and the HIC 100.

In one or more embodiments, the HIC 100 includes an ultra-high frequency (or UHF) tag 210, as illustrated in FIG. 7. Similar to the RFID 200, the UHF tag 210 may be affixed to the front surface 160 or the back surface 180 of the HIC 100, and may be affixed by any suitable adhesive. In some embodiments, the HIC 100 may include an EAS tag 220 and/or an electronic humidity recording tag or inlay. Similar to the RFID 200 and the UHF tag 210, the EAS tag 220 may be affixed to the front surface 160 or the back surface 180 of the HIC 100, or may be between stacked sheets of the HIC 100, and may be affixed by any suitable adhesive. The RFID 200, UHF tag 210, the EAS tag 220, and the electronic humidity recording tag and inlay may be used alone or in combination. In some embodiments, for example, the RFID 200 and the UHF 210 may both be affixed to the front surface 160 of the HIC 100, may both be affixed to the back surface 180 of the HIC 100, one may be affixed to the front surface 160 and the other to the back surface 180 of the HIC 100, may both be embedded between stacked sheets of the HIC 100, or one may be embedded and one may be on the front or back surface 160 or 180 of the HIC 100.

In some embodiments, as illustrated in FIGS. 7 and 8B, the HIC 100 includes an information section 240 where information may be displayed. For example, in one or more embodiments, the front surface 160 of the HIC 100 includes a plurality of parallel lines that provide an area to input personal or other information. In some embodiments, the back surface 180 of the HIC 100 includes the information section 240 including a plurality of parallel lines that provide an area to input personal or other information. The information section 240 allows a user or provider to include contact information so that the product may be returned to the user or provider if it becomes lost, to provide information about a product in the environment the HIC 100 is monitoring, and/or information about the HIC 100, for example, a guide to reading or replacing the HIC 100.

Referring to FIG. 7, in one or more embodiments, the front side 160 of the HIC 100 includes six indicators 120, the label 140 adjacent the indicators 120, the UHF tag 210, the EAS tag 220, and the information section 240. Accordingly, the HIC 100 provides humidity indication, security/inventory tracking, and presents information about the owner, the product and/or the environment the HIC 100 is monitoring, and/or information about the HIC 100.

Referring to FIGS. 8A and 8B, in one or more embodiments, the front side 160 of the HIC 100 includes six indicators 120 and the label 140 adjacent the indicators 120, and the back side 180 of the HIC 100 includes the UHF tag 210 and the information section 240. Accordingly, the HIC 100 provides humidity indication, security/inventory tracking, and presents information about the owner, the product and/or the environment the HIC 100 is monitoring, and/or information about the HIC 100.

Referring to FIG. 9, in one or more embodiments, the front side 160 of the HIC 100 includes six indicators 120, the label 140 adjacent the indicators 120, the UHF tag 210 and the EAS tag 220. Accordingly, the HIC 100 provides humidity indication and security/inventory tracking.

Figure 11:
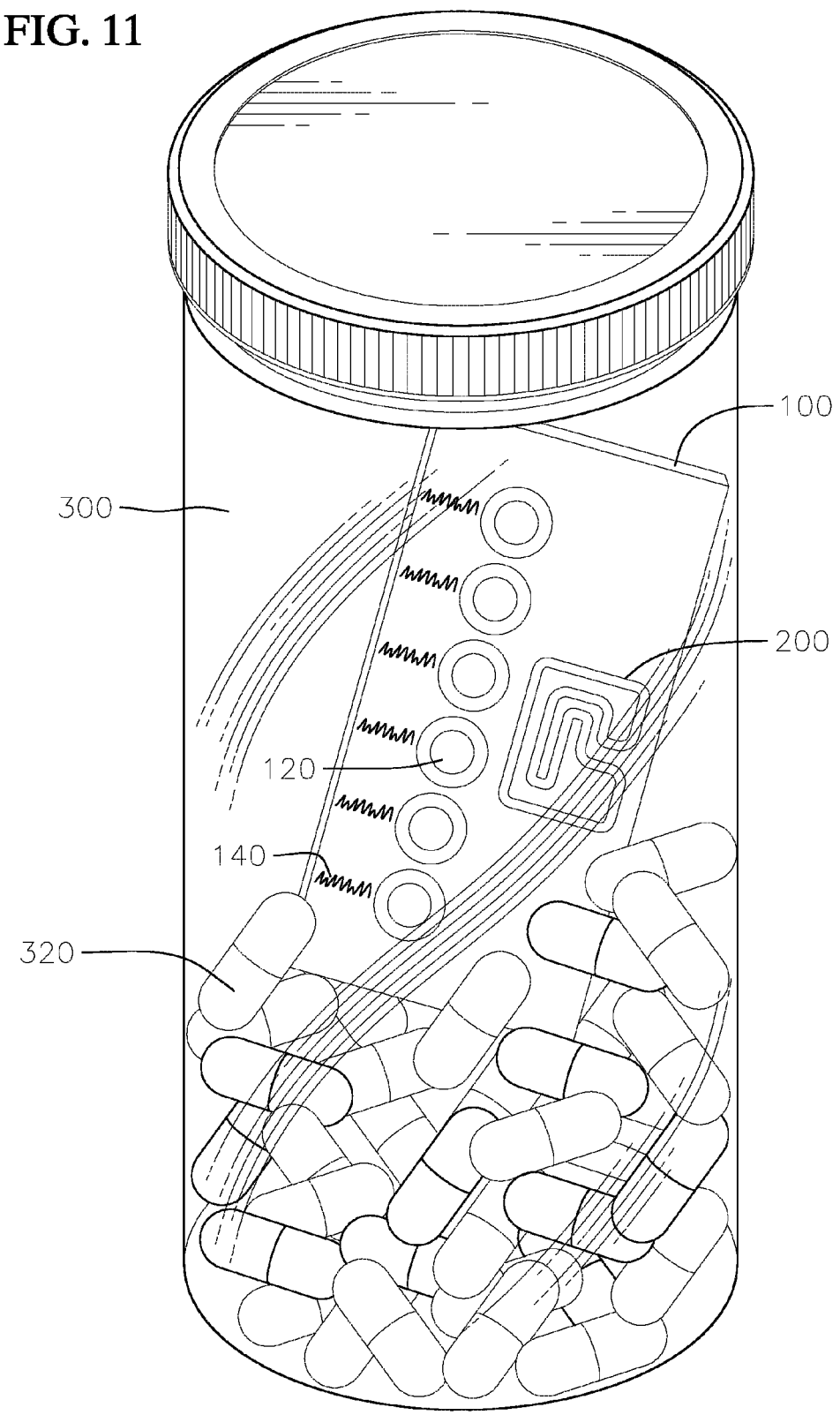
FIG. 11 is a front view of a container containing a product and a humidity indicating card according to one or more embodiments of the present disclosure.

The HIC 100 may be used in a variety of ways. For example, as illustrated in FIG. 11, the HIC 10 may be inserted into the container 300 having a product 320 contained therein. The HIC 100 thus monitors the humidity level inside the container 300 and provides the above-described security and inventory tracking features. Further, in some applications (such as embodiments where the product 320 is tobacco), it may be desirable to continually monitor the humidity level of the environment surrounding the product 320 throughout the life of the product 320. As such, the user will not typically be motivated to discard the HIC 100 until the product 320 is depleted. Further, if the user removes the security tracking device (e.g., the RFID 200), because the HIC 100 is made of a fiber composite, it will be apparent that the HIC 100 has been tampered with. Thus, it is less likely that a user will tamper with the security tracking tag or discard the HIC 100 having the tracking tag, so that it may be possible to track the location of the HIC 100 and the product 320 for a prolonged period of time.

Referring to FIGS. 12A and 12B, as another example, the HIC 100 may be adhered or affixed to a humidity controller, e.g., the humectant system 1. For example, the HIC 100 may be adhered to a front surface or a back surface of the humectant bag 10. The HIC 100 may be affixed or adhered to the humectant bag 10 by an adhesive 18. The adhesive 18 may be any suitable adhesive, including glue, hot melt adhesive (or hot glue), single-sided tape, double-side tape, and/or adhesive backing. In one or more embodiments, the HIC 110 is adhered to the humectant bag 10 by hot melt adhesive. The hot melt adhesive is well-suited for this application because it is able to withstand possible changes in temperature and relative humidity without significantly losing efficacy. Further, the hot melt adhesive provides a secure connection between the humectant bag 10 and the HIC 100. The adhesive 18 may be applied to back edges and corners of the HIC 100 to effectively form a seal between the HIC 100 and the humectant bag 10, thereby preventing any substances from entering a space between the HIC 100 and the humectant bag 10 after they are adhered to each other. In some embodiments, the adhesive 18 is a hot melt adhesive having a 0.45 inch diameter applied by a 50 W glue gun. In addition, the adhesive 18 may serve as a barrier between the HIC 100 and the humectant bag 10 (and the humectant material 14 contained therein). Without the use of a suitable adhesive 18, the HIC 100 may provide a reading that more closely resembles the humidity level inside of the humectant bag 10 instead of the humidity level of the environment outside of and surrounding the humectant bag 10. As such, the adhesive 18 may also serve as a barrier between the HIC 100 and the humectant bag 10 to reduce or minimize the likelihood of an inaccurate reading from the HIC 100.

Although reference is made to embodiments where the humidity controller is the humectant system 1, in some embodiments, the humidity controller is a desiccant, an oxygen scavenger, and/or a humectant. It will be appreciated that the same considerations regarding use of an adhesive for affixing the HIC 100 to a humidity controller including the humectant system 1 may be the same or similar as considerations related to affixing the HIC 100 to a humidity controller that is a desiccant, an oxygen scavenger, and/or a humectant. As such, a suitable adhesive 18 may be used to reduce the likelihood of inaccurate readings based on proximity of the HIC 100 and the desiccant, oxygen scavenger, and/or humectant, and the adhesive 18 may be placed to reduce the likelihood of product becoming entrapped between the HIC 100 and the desiccant, oxygen scavenger, and/or humectant.

While this disclosure has been described in detail with particular references to some exemplary embodiments thereof, the exemplary embodiments described herein are not intended to be exhaustive or to limit the scope of the disclosure to the exact forms disclosed. It is understood that the drawings are not necessarily to scale. Persons skilled in the art and technology to which this disclosure pertains will appreciate that alterations and changes in the described structures and methods of assembly and operation can be practiced without meaningfully departing from the principles, spirit, and scope of this disclosure, as set forth in the following claims and their equivalents.

What is claimed is:

1. A humidity control system comprising:
    a humectant material comprising:
        a viscous miscible glycerol; and
        water;
    an oxygen absorbing composition;
    a package housing the humectant material and the oxygen absorbing composition; and
    a coating coated on an inner surface of the package and between the package and the humectant material and the oxygen absorbing composition, the coating comprising polyethylene, oriented polystyrene, a porous polyethylene resin, polyurethane, a polyether block amide, and/or a polymeric mixture comprising a hydrophilic monomer.

2. The humidity control system of claim 1, wherein the package defines a single cavity that houses the humectant material and the oxygen absorbing composition.

3. The humidity control system of claim 1, wherein the coating has a thickness from between about 0.001 inch and about 0.01 inch.

4. The humidity control system of claim 1, wherein the package comprises kraft paper having a basis weight of 30 lbs/msi.

5. The humidity control system of claim 1, wherein the package comprises an elastomeric polymer.

6. The humidity control system of claim 1, wherein the oxygen absorbing composition comprises:
    a fatty oil; and
    a transition metal enhancer.

7. The humidity control system of claim 6, wherein the transition metal enhancer comprises chromium, manganese, cobalt, iron, copper, and/or zinc.

8. The humidity control system of claim 6, wherein the fatty oil comprises an unsaturated fatty acid.

9. The humidity control system of claim 8, wherein the unsaturated fatty acid comprises an oleic acid and/or a linoleic acid.

10. The humidity control system of claim 6, wherein the fatty oil comprises a vegetable oil comprising triglycerides.

11. The humidity control system of claim 10, wherein the vegetable oil comprises linseed oil, soybean oil, and/or flaxseed oil.

12. The humidity control system of claim 1, wherein the humectant material further comprises a gelling agent.

13. The humidity control system of claim 12, wherein the gelling agent comprises gelatin, xanthan, alginate, and/or pectin.

14. The humidity control system of claim 1, further comprising lemon oil.

15. The humidity control system of claim 1, further comprising a humidity indicating card affixed to a surface of the package.

16. The humidity control system of claim 1, wherein the coating comprises the polyether block amide.

* * * * *